United States Patent [19]

Folden et al.

[11] Patent Number: 5,711,883
[45] Date of Patent: Jan. 27, 1998

[54] METHOD FOR TESTING DIALYZER INTEGRITY PRIOR TO USE

[75] Inventors: Thomas I. Folden, Alamo, Calif.; Hans D. Polaschegg; Harald Peter, both of Oberursel, Germany

[73] Assignee: Fresenius USA, Inc., Lexington, Mass.

[21] Appl. No.: 534,375

[22] Filed: Sep. 27, 1995

[51] Int. Cl.⁶ .......................... B01D 61/24; B01D 65/10
[52] U.S. Cl. ........................... 210/646; 73/40; 604/4
[58] Field of Search ...................... 210/85, 90, 96.2, 210/321.6, 321.65, 646, 739, 741, 929; 604/4–6; 73/38, 40, 866, 40.5 R

[56] References Cited

U.S. PATENT DOCUMENTS

| | | | |
|---|---|---|---|
| 3,416,664 | 12/1968 | Kumme et al. | 210/87 |
| 3,731,680 | 5/1973 | Wright et al. | 210/646 |
| 3,814,249 | 6/1974 | Eaton | 210/86 |
| 3,827,975 | 8/1974 | Bizot et al. | |
| 3,832,067 | 8/1974 | Kopf et al. | 356/181 |
| 3,853,756 | 12/1974 | Stana | 210/23 |
| 3,900,396 | 8/1975 | Lamadrid | 210/94 |
| 3,908,653 | 9/1975 | Kettering | |
| 3,920,030 | 11/1975 | Mason | 604/4 |
| 3,926,561 | 12/1975 | Lucero | |
| 3,939,069 | 2/1976 | Granger et al. | 210/22 A |
| 3,979,284 | 9/1976 | Granger et al. | 210/22 A |
| 3,990,973 | 11/1976 | Boag et al. | 210/87 |
| 4,017,190 | 4/1977 | Fischel | |
| 4,060,485 | 11/1977 | Eaton | 210/87 |
| 4,081,372 | 3/1978 | Atkin et al. | 210/94 |
| 4,085,047 | 4/1978 | Thompson | |
| 4,094,775 | 6/1978 | Mueller | 210/646 |
| 4,153,554 | 5/1979 | von der Heide et al. | |
| 4,181,610 | 1/1980 | Shintani et al. | 210/85 |
| 4,229,290 | 10/1980 | Raj | 210/646 |
| 4,303,068 | 12/1981 | Zelman | |
| 4,331,540 | 5/1982 | Witsoe | 210/646 |
| 4,366,051 | 12/1982 | Fischel | 210/96.2 |
| 4,384,474 | 5/1983 | Kowalski | 73/38 |
| 4,412,553 | 11/1983 | Kopp et al. | 137/118 |
| 4,444,596 | 4/1984 | Gortz et al. | 134/18 |
| 4,444,597 | 4/1984 | Gortz et al. | 134/18 |
| 4,449,392 | 5/1984 | Huschke | 73/40 |
| 4,496,458 | 1/1985 | Lee | 210/90 |
| 4,517,081 | 5/1985 | Amiot et al. | 210/85 |
| 4,614,109 | 9/1986 | Hofmann | 73/38 |
| 4,623,450 | 11/1986 | Vantard et al. | 210/87 |
| 4,680,122 | 7/1987 | Barone | 210/637 |
| 4,702,829 | 10/1987 | Polaschegg et al. | 210/195.2 |
| 4,708,802 | 11/1987 | Rath et al. | 210/641 |
| 4,715,959 | 12/1987 | Allan et al. | 210/637 |
| 4,762,618 | 8/1988 | Gummesson et al. | 210/637 |
| 4,846,970 | 7/1989 | Bertelsen et al. | 210/232 |
| 4,861,485 | 8/1989 | Fecondini | 210/641 |
| 4,872,974 | 10/1989 | Hirayama et al. | 210/90 |
| 5,064,529 | 11/1991 | Hirayama et al. | 210/90 |
| 5,487,827 | 1/1996 | Peterson et al. | 604/4 |

FOREIGN PATENT DOCUMENTS

3442744 C2   7/1988   Germany.

OTHER PUBLICATIONS

Fresenius AG, "Method for Testing a Hemodialysis Membrane.", date unknown.

*Primary Examiner*—Joseph W. Drodge
*Attorney, Agent, or Firm*—Davis, Graham & Stubbs LLP

[57] ABSTRACT

The present invention includes a method and apparatus for the testing the integrity of a dialyzer prior to use. The dialyzer is tested on the same hardware used for the treatment of dialysis. The dialysate and blood sides of the dialyzer are primed in the normal manner. The blood and saline lines are clamped while the venous line is vented to the atmosphere. The ultrafiltrate flow rate is increased until the blood side fluid is ultrafiltered. The dialysate side is monitored for pressure increases. If the pressure does not increase, the test fails.

8 Claims, 3 Drawing Sheets

METHOD FOR TESTING DIALYZER INTEGRITY PRIOR TO USE

FIELD OF THE INVENTION

Described herein is a method for the detection of blood leaks on a dialyzer prior to use. More specifically, a method and apparatus, using existing dialysis treatment equipment, for automatically testing a dialyzer membrane for material integrity leaks prior to reusing the dialyzer is disclosed.

BACKGROUND OF THE INVENTION

Hemodialysis is a form of treatment for chronic kidney failure. With hemodialysis, the patient's blood is purified outside the body in an artificial kidney called a dialyzer. A dialyzer contains a blood compartment and a dialysate compartment separated by a membrane. The total surface area of the membrane measures 1-2 square meters. During a hemodialysis treatment the patient's blood is allowed to flow on one side of the membrane and dialysis fluid on the other. At the beginning of the dialysis treatment, the waste product level in the blood is high, while the dialysis fluid contains no such products. Since the waste products are usually small dissolved substances they are able to move from the blood through the membrane and into the dialysis fluid. This movement continues until there is an equal level of the substances on both sides of the membrane.

In order to remove excess water from the blood, it is necessary to create a pressure difference between the blood side and the dialysis fluid side of the membrane. The process of creating this pressure between the two sides of the membrane is called ultrafiltration.

Hemodialysis using disposable dialyzers became an extensively used method for performing dialysis treatment. One example of a widely used dialyzer of this type is the hollow fiber dialyzer, having a blood compartment composed of a bundle of hollow fibers and a dialysate compartment formed by a sleeve surrounding the fiber bundle. Treatment using disposable dialyzers, however, may be plagued with extremely high costs.

Efforts undertaken to reduce the costs associated with dialysis treatment concluded that disposable, hollow fiber dialyzers may be reused provided that they are adequately cleansed of bacterial, protein and other particulate matter. It is readily understood that the cleansing process as well as usage of the dialyzer may cause damage to the dialyzer. The cleansed dialyzer must be tested for leakage between the blood and the dialysate compartment caused by broken fibers or broken seals.

The importance of ensuring the integrity of a dialyzer prior to its use or reuse is readily understood. If there is an integrity leak in the membrane, one can either infuse non sterile dialysate into the patient or lose blood into the dialysate stream depending on the pressure gradients in the dialyzer.

As indicated by the prior art, special machines for preparing dialyzers for reuse have been developed which often include testing means for testing leakage and dialyzing capability. For example, U.S. Pat. No. 4,846,970 of Bertelsen et al. discloses a cross-flow membrane test unit. The device of this invention has a bottom cell body, a top cell body and a pair of laterally spaced O-rings forming a seal in between. The bottom cell body is provided with a feed spacer cavity and the top cell body is provided with a permeate carrier cavity. A test sample of the membrane is placed on the machine, and the flow dynamics of a full scale dialysis system are simulated.

U.S. Pat. Nos. 4,444,596 and 4,444,597 of Gortez et al. disclose an automated method and apparatus for cleaning and disinfecting dialyzers prior to reuse, having multiple stations simultaneously capable of cleaning a plurality of dialyzers. By using the separate machine of this invention, the dialyzer, station cleaning the dialyzer and the patient are identified and the identifications are stored in memory. The cleaning procedures are automatically machine sequenced, and the sequence is selectively controlled using test procedures measuring indicia of dialyzer reusability. Test procedures on the machine include a blood presence test, a pressure leakage test, and an ultrafiltration rate test.

U.S. Pat. No. 4,449,392 of Huschke teaches a device for testing sterile filters. The filter testing device of this invention includes a filter housing that has an air inlet, outlet, and receives the filter. An inlet line is connected to the air inlet. An inlet valve for the inlet line is controlled to produce a continuous and evenly increasing air pressure therein, and an electronic pressure sensor monitors the air pressure therein. An electronic evaluating and control circuit has a time switch, an adjustable threshold device and a peak pressure detector, and controls the inlet valve, a vent valve connected to the inlet line, and a recording mechanism. The air pressure in the inlet line is increased until it reaches a preset pressure. The inlet valve is then closed for the time period set on the time switch. Thereafter, air is again supplied to the inlet line until no further pressure increases are detected by the peak pressure sensor.

U.S. Pat. No. 5,064,529 of Hirayama et al. discloses an apparatus for testing membrane filters. The membrane filter testing apparatus of this invention uses a control circuit for increasing the pressure at the primary side of a membrane filter. The control circuit is fixedly accommodated in a housing and wetted with a liquid. The pressure at the primary side is increased by gas at a predetermined rate. The pressure at the primary side is checked after the lapse of a predetermined period of time to see if it is within a specified range.

Although the prior art has made advances in ways to reduce costs associated with dialysis treatment by developing machines which test dialyzer integrity before reuse, the machines themselves are costly. An operator is needed to program the machine, place the dialyzer on the machine, evaluate the output, and perform whatever other maintenance functions the particular machine requires.

A further limitation for testing dialyzers in this fashion is that the dialyzer is tested in an environment apart from the environment in which it is used. Testing the dialyzer as part of the cleaning process does not take into account that the cleaning or preparation process itself may damage the membrane.

A desired method for testing membrane integrity would test the dialyzer on the same machine and in the same environment in which the dialyzer is used. It would test the integrity of the membrane just prior to the dialyzer being used, and would utilize existing equipment currently used for hemodialysis treatment, thus being cost efficient for the user.

SUMMARY OF THE INVENTION

The present invention provides a method and apparatus for testing the integrity of a dialyzer prior to its use. The method of this invention provides an advantage over the prior art in that it can be performed in conjunction with existing hardware used in the treatment of dialysis. No special machines, valves or pressurized gas is required.

Although described in terms of testing the integrity of a dialyzer prior to its reuse, it is readily understood that the method of this invention can be practiced on all dialyzers, not just reused dialyzers.

A further advantage of the method of the present invention is that it may be performed just prior to commencing dialysis treatment. Often, separate machines, such as those found in the prior art, cleanse, sterilize and test the dialyzer before its use and do not take into account that the cleansing or moving process may also cause damage to the dialyzer. Damage may still occur even after the dialyzer has been tested and determined to be functioning well.

The method of the present invention includes the following general steps. First, the dialyzer is primed in the normal manner. The blood side is primed with a saline solution and the dialysate side is primed with a saline solution. Once primed, the blood lines and the saline lines are clamped. The venous line is vented to the atmosphere through the venous pressure line transducer protector which keeps the blood side sterility intact.

Next, the ultrafiltrate flow rate is increased to maximum. The blood side prime volume is ultrafiltered through the membrane and eventually replaced by air which has entered the circuit via the transduced protector.

The pressure on the dialysate side is then checked. Since air cannot pass through an intact membrane, as more air enters the blood compartment and less priming fluid is available to meet the demand of the ultrafiltrate flow rate, the transmembrane pressure increases. Therefore, if the transmembrane pressure has increased, the membrane is intact and can be used for treatment. If, on the other hand, the pressure on the dialysate side has not increased, then air must have passed through the membrane and the dialysate machine cannot increase the pressure since the loop is open to the atmosphere.

DETAILED DESCRIPTION OF THE PREFERRED EMBODIMENTS

Figure 1:
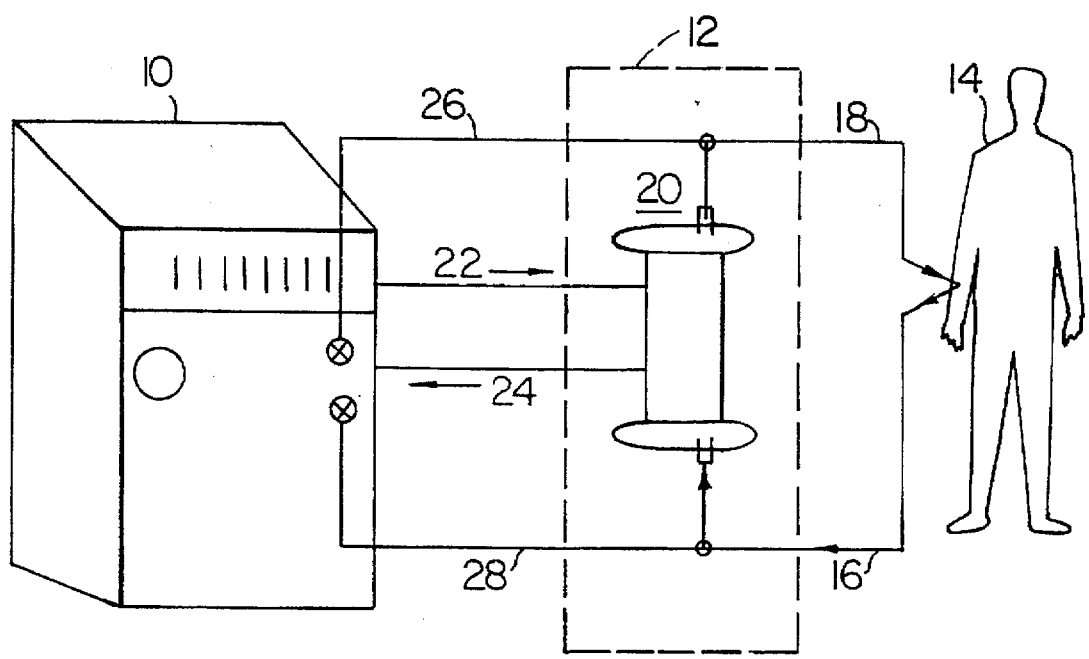
FIG. 1 is a schematic representation showing the components of hemodialysis delivery system.

With reference to FIG. 1, it can readily be seen that the practice of the method of this invention requires no additional equipment, and may readily be practiced using standard hemodialysis treatment equipment programmed for the test procedure. The method of the present invention is performed using the following apparatus: a dialysis controller 10, a dialyzer 12, and bloodlines (16 and 18).

Generally, the controller 10 performs the basic function of regulating the flow rate, pressure and temperature of the dialysate. Standard features of controllers include a blood pump, heparin pump, an air detector, a blood leak detector, a dialysate fluid pump, monitors for blood, dialysis fluid and ultrafiltration, plus alarm circuits and automatic shut off.

The dialyzer 12 consists of a blood compartment, a dialysate compartment and a membrane which separates the two. The total surface area of the membrane measures 1 to 2 square meters. The membrane is a thin film with thousands of small holes that allow water and small dissolved substances to pass through, but retain proteins and blood cells, which are too large to pass through the membrane. During dialysis ultrafiltration, hydrostatic pressure is exerted across the dialyzer membrane causing the removal of excess fluid from the bloodstream.

Dialysis bloodlines (16 and 18) function to connect the patient to the pump and dialyzer, providing a reliable path for blood from and to the access site 14. An arterial bloodline 16 takes blood to the dialyzer while the venous bloodline 18 takes blood back to the patient.

Figure 2:
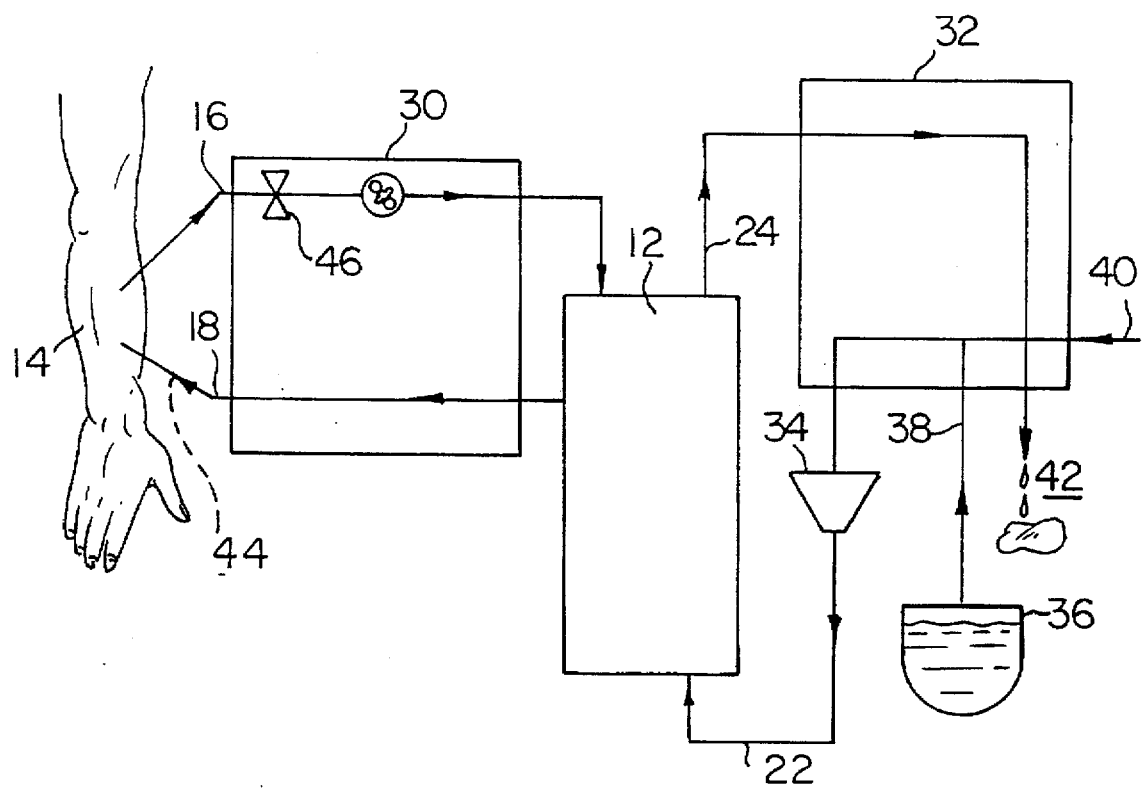
FIG. 2 is a circuit diagram showing the preferred embodiment of the flow circuit of the invention

Practice of the method of the present invention is readily understood with reference to FIG. 2. The dialyzer 12 is primed with saline in the normal way it is primed before initiating hemodialysis treatment. Once primed, the arterial bloodline 16 is clamped with clamp 46. The venous bloodline 18 is vented to the atmosphere 44 through the venous pressure line transducer 26. The venous pressure line transducer 26, which can be seen with reference to FIG. 1, keeps the sterility of the blood side of the dialyzer 12 intact.

Resuming the discussion with FIG. 2, the ultrafiltrate flow rate 22 is increased to a maximum of 3000 ml/hr. At this point, the blood side prime volume is ultrafiltered through the membrane. Since the venous bloodline 18 is vented to the atmosphere 44, air now enters the circuit through the transducer protector 26 and fills the blood side of the dialyzer 12 where the blood side prime had previously been.

Once the blood side prime is gone, the transmembrane pressure is checked. In an intact membrane, air cannot pass through the membrane, so as more air enters the blood compartment and less priming fluid is available to meet the demands of the ultrafiltrate flow rate, the transmembrane pressure increases to a value greater than 300 mmHg.

Figure 3:
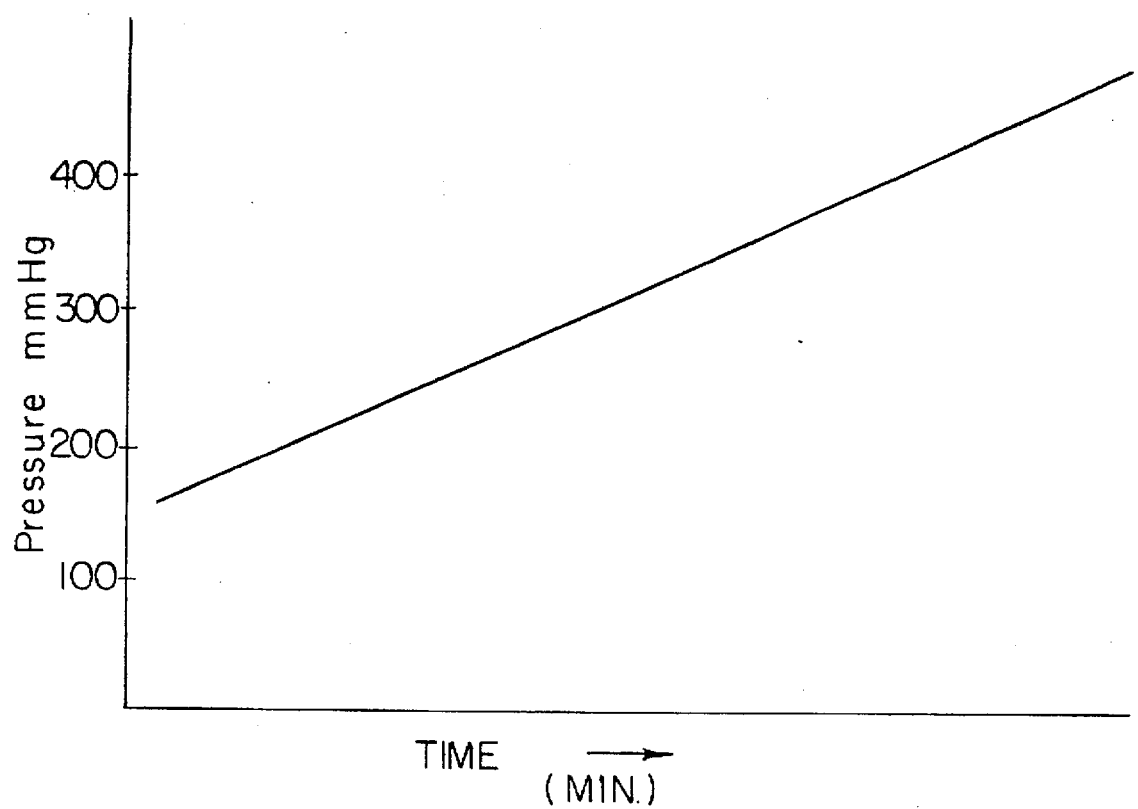
FIG. 3 is a graph showing an example of the pressure gradients of the dialysis circuit for a successful test.
Figure 4:
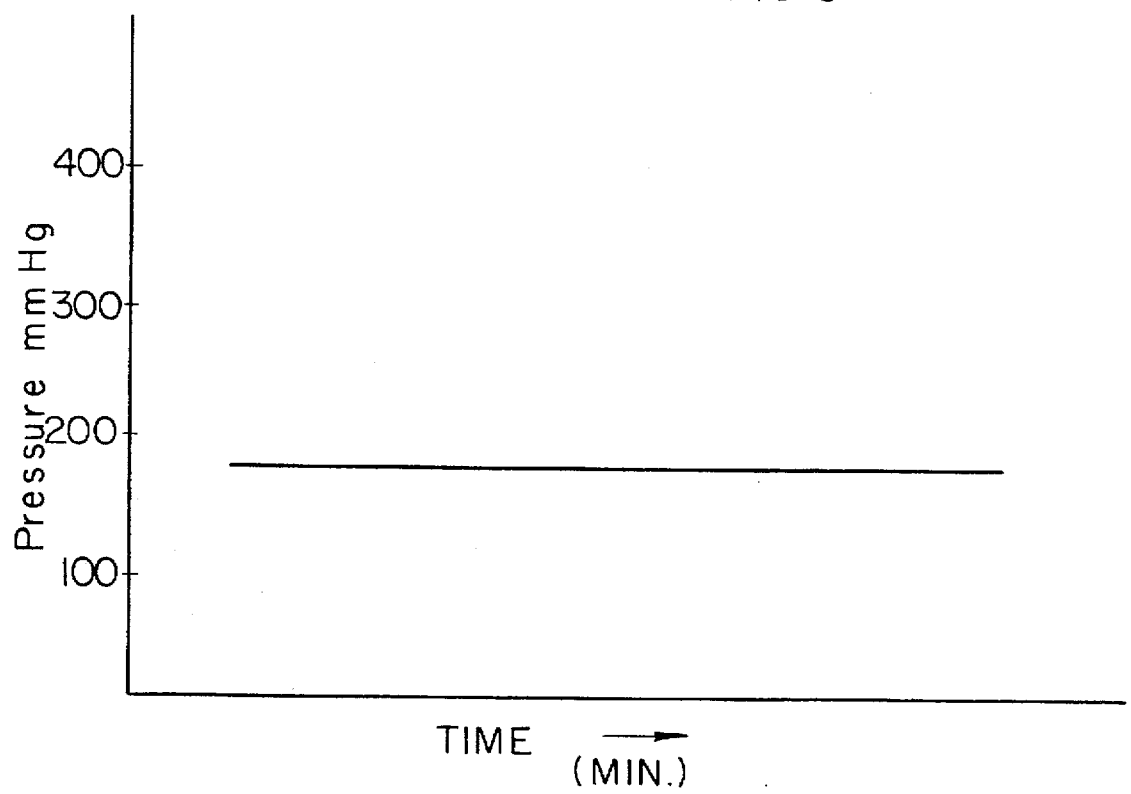
FIG. 4 is a graph showing an example of the pressure gradients of the dialysis circuit for an unsuccessful test.

If the dialysate side pressure has increased, the integrity of the dialyzer is confirmed and the dialyzer may be reused for dialysis treatment. This result can be seen with reference to FIG. 3. If the transmembrane pressure has not increased, then it is most probable that the dialyzer has a material integrity leak and should not be used. This result is depicted by FIG. 4.

Figure 5:
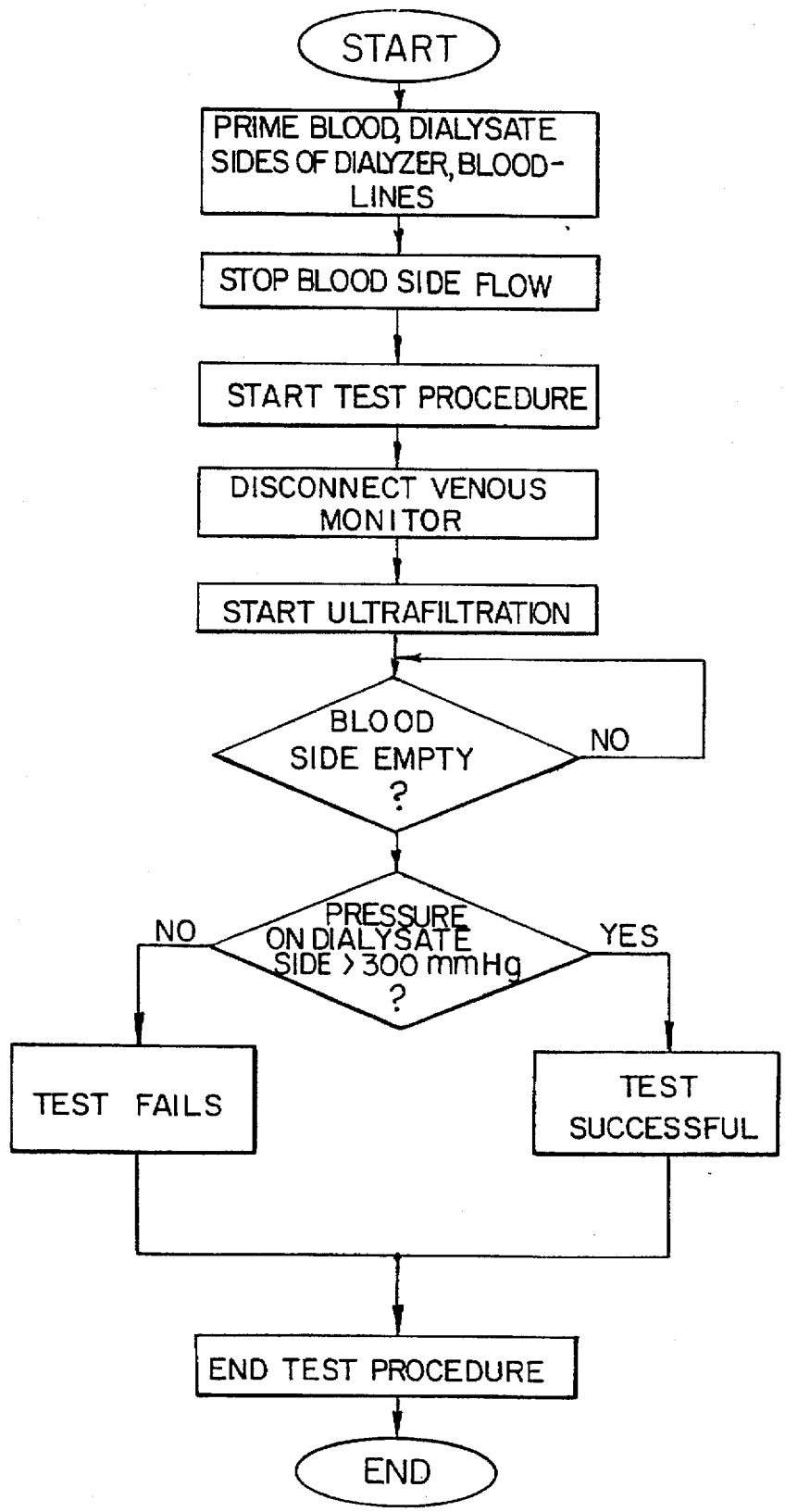
FIG. 5 is a flow chart showing the preferred embodiment of the method of this invention.

In use, the method of this invention works generally as follows, as depicted in FIG. 5: While between patients scheduled to receive dialysis treatment, a nurse or technician working at that particular station primes the blood side and the dialysate sides of the dialyzer as well as the attached lines with saline in the normal manner. The nurse or technician then stops the blood side flow to the dialyzer. Next, the nurse or technician presses the test button on the machine to perform the test that will evaluate the integrity of the dialyzer. The venous pressure monitor line is removed from the machine. The transmembrane pressure is checked by the machine's standard pressure control mechanisms. If the transmembrane pressure has increased, the nurse or technician knows that the dialyzer is able to be reused. If the pressure on the dialysate side has not increased, the test fails and the nurse or technician knows that the dialyzer can not be used for further treatment.

We claim:

1. A method for testing dialyzer integrity prior to use, comprising: preparing a hemodialysis delivery system for hemodialysis treatment on a patient, said hemodialysis delivery system including a dialyzer; testing said dialyzer for leaks; and performing hemodialysis treatment on said patient, wherein said testing step is comprised of: connecting a first end of a venous bloodline to said dialyzer; connecting a first end of an arterial bloodline to said dialyzer; venting said second end of said venous bloodline to the atmosphere; clamping a second end of said arterial bloodline; increasing flow of dialysate through the dialysate side of the dialyzer from a first flow rate to a second flow rate; and testing the transmembrane pressure to determine if a leak in the membrane has occurred.

2. The method of claim 1, wherein the flow of dialysate through the dialysate side of the dialyzer is increased to a value greater than 3000 ml/hour.

3. The method of claim 2, wherein the transmembrane pressure is compared to a value of 300 mmHg, and further includes the step, after said testing step, of discarding the membrane if the transmembrane pressure is less than 300 mmHg.

4. The method of claim 3, further comprising the step, before said testing step, of priming the blood side compartment with saline solution.

5. The method of claim 4, further comprising the step, before said testing step, of priming the dialysate side compartment with saline solution.

6. A method for testing a dialyzer for leaks comprising the steps of: engaging with a dialysis patient a hemodialysis delivery system having a dialysis control unit with means to test a transmembrane pressure, a dialyzer having a dialysate compartment, a blood compartment and a membrane therebetween, a venous bloodline having a first and second end, and an arterial bloodline having a first and second end; performing hemodialysis treatment on said patient; testing the dialyzer in the hemodialysis delivery system; and performing hemodialysis on a second patient using the same hemodialysis delivery system if the dialyzer passes the test; and before said testing step, priming the dialysate compartment and blood compartment with saline solution, using saline lines.

7. The method of claim 6, wherein said testing step is comprised of the steps of: attaching the first end of the venous bloodline to the dialyzer; attaching the first end of the arterial bloodline to the dialyzer; clamping the bloodline and its respective saline line; venting the venous line; increasing ultrafiltrate flow rate; and checking the transmembrane pressure to determine if there is a leak in the membrane.

8. The method of claim 7, wherein the transmembrane pressure is compared to a value no less than 300 mmHg, and further comprising the step, after said testing step, of discarding the membrane if the value of the transmembrane pressure is less than 300 mmHg.

* * * * *